US00PP08478P

United States Patent [19]

Fiala, deceased et al.

[11] Patent Number: Plant 8,478

[45] Date of Patent: Nov. 30, 1993

[54] FLOWERING CRAB APPLE TREE 'PURPLE PRINCE'

[75] Inventors: John L. Fiala, deceased, late of Medina, Ohio; by Eline E. Kleiss, personal representative, Ocala, Fla.

[73] Assignee: J. Frank Schmidt & Son Co., Boring, Oreg.

[21] Appl. No.: 860,773

[22] Filed: Mar. 27, 1992

[51] Int. Cl.[5] ..... A01H 5/00

[52] U.S. Cl. ..... Plt./35.2

[58] Field of Search ..... Plt./35.2

*Primary Examiner*—James R. Feyrer
*Assistant Examiner*—Erich E. Veitenheimer
*Attorney, Agent, or Firm*—Klarquist, Sparkman, Campbell, Leigh & Whinston

[57] ABSTRACT

A new variety of flowering crab apple tree, which I call 'Purple Prince', has bright red single flowers, is resistant to apple scab, has purple tinted foliage and purple fruit, and exhibits an unusually vigorous rate of growth.

2 Drawing Sheets

DESCRIPTION

The present invention relates to a new and distinct variety of flowering crab apple tree which I have named 'Purple Prince'.

My new "Purple Prince' variety originated out of a breeding program as a cross of Malus (Malus 'Bluebeard'×Malus 'Liset')×Malus 'Garnet'. My attention was first directed to this plant because of its combination of purple foliage, disease resistance, and purple fruit.

I observed my new variety for a number of years growing in a cultivated area on my Falconskeape Farm in Medina, Ohio. My observations have confirmed that my variety is a distinct and unusual cultivar. Subsequent asexual propagation of my variety by budding under my direction at the nursery of J. Frank Schmidt & Son, Co., in Boring, Ore., and observation of the resulting progeny has proven the characteristics of my new variety to be fixed. Furthermore, these observations have confirmed that my new variety represents a new and improved variety of flowering crab apple tree, as particularly evidenced by the following unique combination of characteristics, which have proven firmly fixed, are outstanding therein, and which distinguish it from all of the varieties of this species of which I am aware:

1. Resistance of foliage and purple fruit to apple scab;
2. Bright red single flowers;
3. Unusually vigorous growth; and
4. Purple tinted foliage.

The accompanying photographs depict the color of the blooms, fruit and foliage of my new variety, as well as the shape of the tree, as nearly true as is reasonably possible to make the same in a color illustration of this character.

Figure 2:
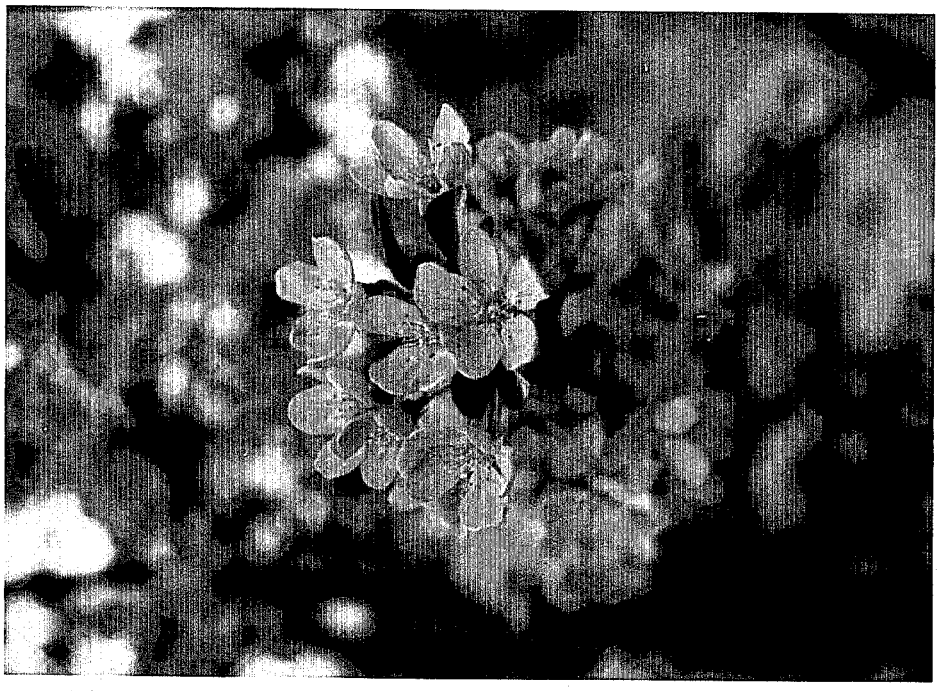
FIG. 2 is a color photograph of flowers of the tree of the present invention.
Figure 1:
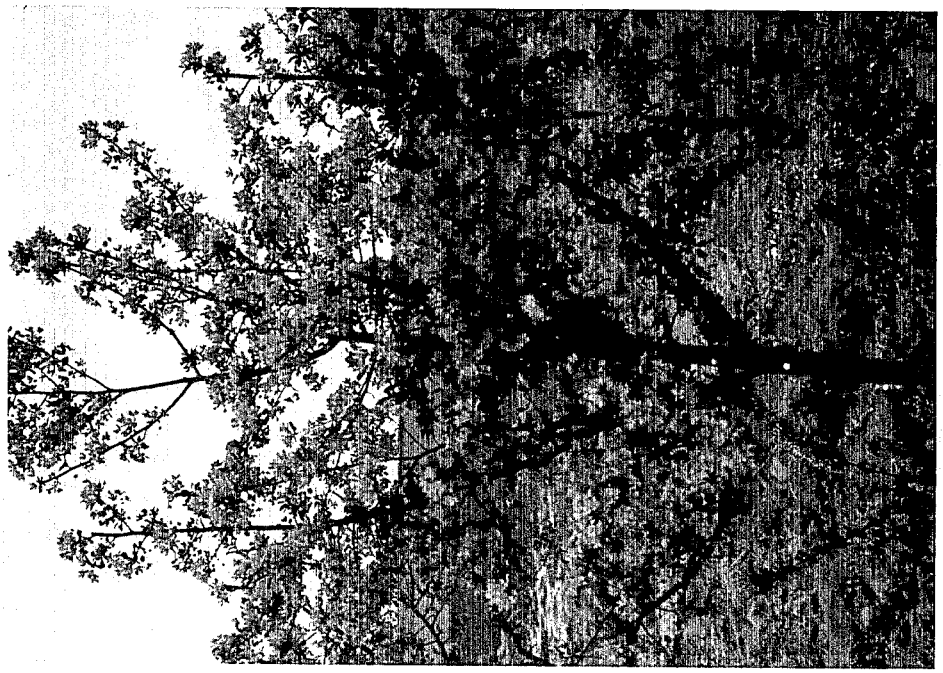
FIG. 1 is a color photograph of a tree of the present invention.
Figure 3:
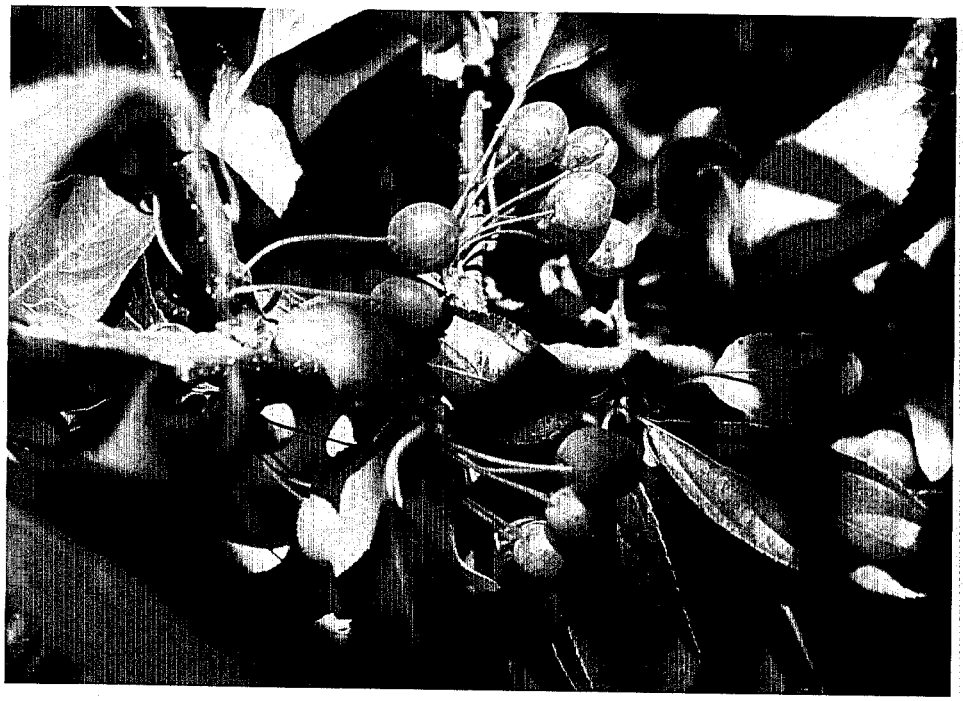
FIG. 3 is a color photograph of fruit of the tree of the present invention.
Figure 4:
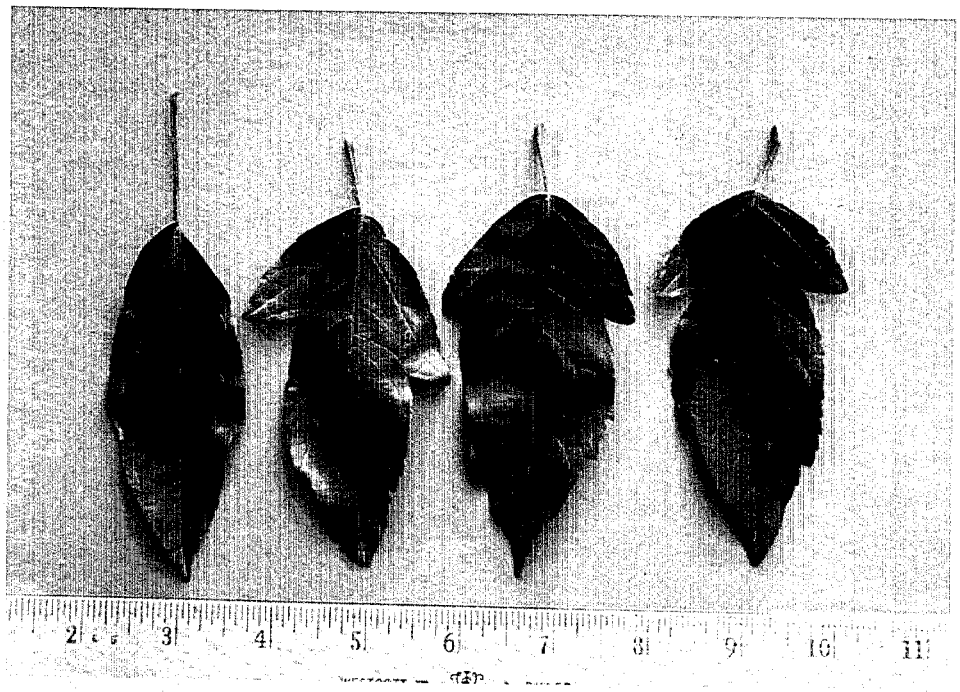
FIG. 4 is a color photograph of leaves of the tree of the present invention.

My new variety of tree differs from the parent cultivars in a number of respects. The variety Malus 'Bluebeard' is a selection used in my breeding program which has never been released. The Malus 'Bluebeard' cultivar has proven to be highly susceptible to apple scab while my new 'Purple Prince' cultivar is resistant to apple scab. In addition, my new variety has a single flower while the Malus 'Bluebeard' variety has a semi-double flower.

In comparison to my new cultivar, the Malus 'Liset' variety is a slower growing tree which exhibits less height, stem caliper, and fewer branches on one year old stems than my new variety. The Malus 'Liset' cultivar also develops vertical stem splits in its bark which are resisted by my new variety. In addition, leaves of vigorous shoots of my new variety commonly have two basal lobes while those of the Malus 'Liset' cultivar generally do not.

In addition, the Malus 'Garnet' cultivar has green leaves, red fruit and white flowers in comparison to the purple-tinted leaves, purple fruit and red flowers of my new variety.

Also, in comparison to the commercially available Malus 'Prairifire' variety, my new variety of flowering crab apple tree is faster growing and has more branches as a one-year old tree in comparison to the 'Prairifire' cultivar. In addition, my 'Purple Prince' variety generally has larger fruit (about 1.4 centimeters on average) than the fruit of the 'Prairifire' cultivar (about 1.0 centimeters on average). Also, the fruit of my new variety is a purplish color (like purple RHS 185 A) in comparison to the red fruit of the 'Prairifire' variety (like red RHS 46 A - 46 B). In addition, the leaves of vigorous shoots of my new 'Purple Prince' variety commonly have two basal lobes while those of the 'Prairifire' cultivar do not.

The following comparison table illustrates observed differences in growth rate between 'Purple Prince', 'Liset' and 'Prairifire' varieties of flowering crab apple trees growing in Boring, Ore.

| | 'Purple Princes' | 'Liset' | 'Prairifire' |
|---|---|---|---|
| Average height, 1 yr tree | 188 cm | 168 cm | 176 cm |
| Average number of branches on 1 yr tree | 3.9 | 3.2 | 2.1 |
| Average stem diameter of 2 yr tree, 6" | 2.64 cm | 2.39 cm | 2.00 cm |

-continued

| | 'Purple Princes' | 'Liset' | 'Prairifire' |
|---|---|---|---|
| above ground | | | |

The following is a detailed description of my new variety of Malus 'Purple Prince' flowering crab apple tree, with color terminology in accordance with The Royal Horticultural Society Color Chart (hereinafter RHS) published by The Royal Horticultural Society of London.

Parentage: Malus ('Bluebeard'×'Liset')×Malus 'Garnet'

Propagation: Holds to distinguishing characteristics through succeeding propagation by budding.

Locality where grown and observed: Medina, Ohio, and Boring, Ore.

Tree: Strong upright growing branches spread to form a rounded canopy as the tree matures.

Vigor: Vigorous, being faster growing than the majority of commercial crab apple cultivars. In the Northwest Oregon locale, one year old budded trees have been observed to grow 1.9 meters while other crab apple cultivars grow one to two meters.

Growth rate: Six year old trees growing in Northwest Oregon have been observed to be 4 meters in height. At this stage, terminal growth elongation averages 50 cm per year.

Foliage:

*Size.*—9.0–12.0 cm long by 5.0–7.5 cm wide.

*Shape.*—Ovate, entire or with two small lobes on vigorous shoots.

*Apex.*—Acute to acuminate.

*Base.*—Broadly acute to subcordate.

*Margin.*—Serrate.

*Color.*—Spring new growth is red-purple like RHS 60 A. Late summer leaves are similar to yellow-green like RHS 147 A, but slightly darker.

*Petiole.*—20–30 mm long by 2–3 mm thick, pubescent.

*Stipules.*—Two stipules present to leaf base, 4–15 mm.

Buds: Winter color is grayed-orange like RHS 166 A to grayed-purple like RHS 183 A.

Blooms: Annually.

*Character.*—Single.

*Size.*—3.0–3.5 cm.

*Color.*—Red-purple like RHS 57 B to RHS 58 B.

*Count.*—Average count 5 per spur.

*Petals.*—5 per flower.

Seed: Obovoid, 5 mm×3 mm×2 mm. Seed coat grayed-orange like RHS 176 A to grayed red like RHS 178 A, 5 per fruit.

Fruit:

*Shape.*—Round.

*Size.*—1.4 cm average (1.2–1.5 cm).

*Color.*—*Grayed-purple like RHS* 185 A.

*Count.*—Average count 4.0 per spur.

*Stem length.*—Average fruit stem length 3.0 cm.

*Interior color.*—Purple-red like RHS 60 B.

*Retention.*—Fruit persists on tree until late November in Northwest Oregon.

Ultimate tree size: Unknown at this time as original tree has not yet reached mature size. Based on growth rate and form, it is expected to mature at 6–7 meters tall by 7–8 meters in width.

Ultimate tree shape: Unknown at this time as original tree has not yet reached maturity. Present shape is rounded with a strong branch structure of upright then spreading branches. It is expected that the ultimate shape will be round.

Bark: Young bark (up to approximate 6 year age) smooth, grayed-orange like RHS 176 A to RHS 177 A. Older bark becomes rough-ended, grey-brown like RHS 199 A. Lenticils raised, oblong, 1 mm×2 mm to 1 mm×4 mm, orange-white like RHS 159 B.

Branching habit: Branches are strong, originating at 30 to 60 degree angles from the central trunk, growing upward then spreading outward as branch diameter becomes thinner.

Precocity: Average for a commercial cultvar. Blooms and fruits sparsely in the second year and moderately the third year under Northwest Oregon growing conditions.

It is claimed:

1. A new and distinct variety of flowering crab apple tree substantially as herein shown and described, characterized particularly as to novelty by its resistance to apple scab, its bright red single flowers, purple tinted foliage and purple fruit, and unusually vigorous growth rate.

* * * * *